(12) United States Patent
Dueck et al.

(10) Patent No.: US 12,290,660 B2
(45) Date of Patent: May 6, 2025

(54) HEATING ELEMENTS FOR THERMALLY-DRIVEN PHASE TRANSITION IMPLANTABLE MICROPUMP

(71) Applicant: Cochlear Limited, Macquarie University (AU)

(72) Inventors: Wolfram Frederik Dueck, Hannover (DE); Daniel Smyth, Mechelen (BE); Jonathon Kirk, Centennial (AU)

(73) Assignee: Cochlear Limited, Macquarie University (AU)

( * ) Notice: Subject to any disclaimer, the term of this patent is extended or adjusted under 35 U.S.C. 154(b) by 1011 days.

(21) Appl. No.: 17/274,760

(22) PCT Filed: Dec. 31, 2019

(86) PCT No.: PCT/IB2019/061465
§ 371 (c)(1),
(2) Date: Mar. 9, 2021

(87) PCT Pub. No.: WO2020/144534
PCT Pub. Date: Jul. 16, 2020

(65) Prior Publication Data
US 2022/0047804 A1 Feb. 17, 2022

Related U.S. Application Data

(60) Provisional application No. 62/789,677, filed on Mar. 9, 2021.

(51) Int. Cl.
*A61M 5/142* (2006.01)
*A61F 2/18* (2006.01)
*A61M 5/168* (2006.01)

(52) U.S. Cl.
CPC ........... *A61M 5/14276* (2013.01); *A61F 2/18* (2013.01); *A61M 5/14228* (2013.01);
(Continued)

(58) Field of Classification Search
CPC .......... A61M 5/14276; A61M 5/14228; A61M 5/16804; A61M 2205/3653;
(Continued)

(56) References Cited

U.S. PATENT DOCUMENTS 5,738,658 A 4/1998 Maus et al.
6,200,293 B1 * 3/2001 Kriesel ............. A61M 5/14586
604/153

(Continued)

OTHER PUBLICATIONS

Borkholder et al., "Round Window Membrane Intracochlear Drug Delivery Enhanced by Induced Advection," Journal of Controlled Release, vol. 174, pp. 171-176 (2014).

(Continued)

*Primary Examiner* — Jessica Arble
*Assistant Examiner* — Nhu Q. Tran
(74) *Attorney, Agent, or Firm* — Knobbe, Martens, Olson & Bear, LLP

(57) ABSTRACT

An apparatus includes an enclosure containing a hermetically sealed region, the enclosure configured to be implanted on or within a recipient. The apparatus further includes circuitry within the hermetically sealed region and configured to generate signals. The apparatus further includes at least one heating element configured to receive the signals and to generate heat in response to the signals. The apparatus further includes at least one flow control element outside the hermetically sealed region and configured to respond to the heat by controlling a flow of liquid through at least one cannula to controllably administer the liquid internally to the recipient.

23 Claims, 11 Drawing Sheets

(52) U.S. Cl.
CPC ... *A61M 5/16804* (2013.01); *A61F 2002/183* (2013.01); *A61F 2250/0068* (2013.01); *A61M 2205/3653* (2013.01)

(58) Field of Classification Search
CPC .............. A61M 2210/0662; A61F 2/18; A61F 2002/183; A61F 2250/0068
See application file for complete search history.

(56) References Cited

U.S. PATENT DOCUMENTS

| | | | |
|---|---|---|---|
| 6,203,523 | B1 | 3/2001 | Haller et al. |
| 6,485,462 | B1 | 11/2002 | Kriesel |
| 6,514,285 | B1 * | 2/2003 | Pinchasik ................. A61F 2/95 623/1.22 |
| 2004/0082908 | A1 | 4/2004 | Whitehurst et al. |
| 2009/0306633 | A1 * | 12/2009 | Trovato ................. A61B 1/041 604/891.1 |
| 2014/0058314 | A1 * | 2/2014 | Parker ................. A61N 1/0541 604/20 |
| 2015/0011937 | A1 | 1/2015 | Connelly et al. |
| 2015/0346732 | A1 | 12/2015 | Chappel |
| 2018/0117246 | A1 | 5/2018 | Kim |

OTHER PUBLICATIONS

Forouzandeh et al., "A Nanoliter Resolution Implantable Micropump for Murine Inner Ear Drug Delivery," Journal of Controlled Release, https://doi.org/10.1016/j.jconrel.2019.01.032, in 23 pages (2019).

Forouzandeh et al., "Murine Round Window Membrane Inner Ear Drug Delivery with a Wirelessly Controlled Implantable Micropump," ARO 2018 Conference, in 9 pages (2018).

Johnson et al., "Towards an Implantable, Low Flow Micropump That Uses No Power in the Blocked-Flow State," Micromachines, vol. 7, No. 6, in 16 pages (2016).

Li et al., "Pumping Mechanism of Thermally Driven Phase Transition Micropump," Microscale Thermophysical Engineering, vol. 8, pp. 31-41 (2004).

Tandon et al., "Microfabricated Reciprocating Micropump for Intracochlear Drug Delivery with Integrated Drug/Fluid Storage and Electronically Controlled Dosing," Lab on a Chip, vol. 16, No. 5, pp. 829-846 (2016).

International Search Report and Written Opinion received in PCT Application No. PCT/IB2019/061465 mailed on Apr. 22, 2020 in 10 pages.

* cited by examiner

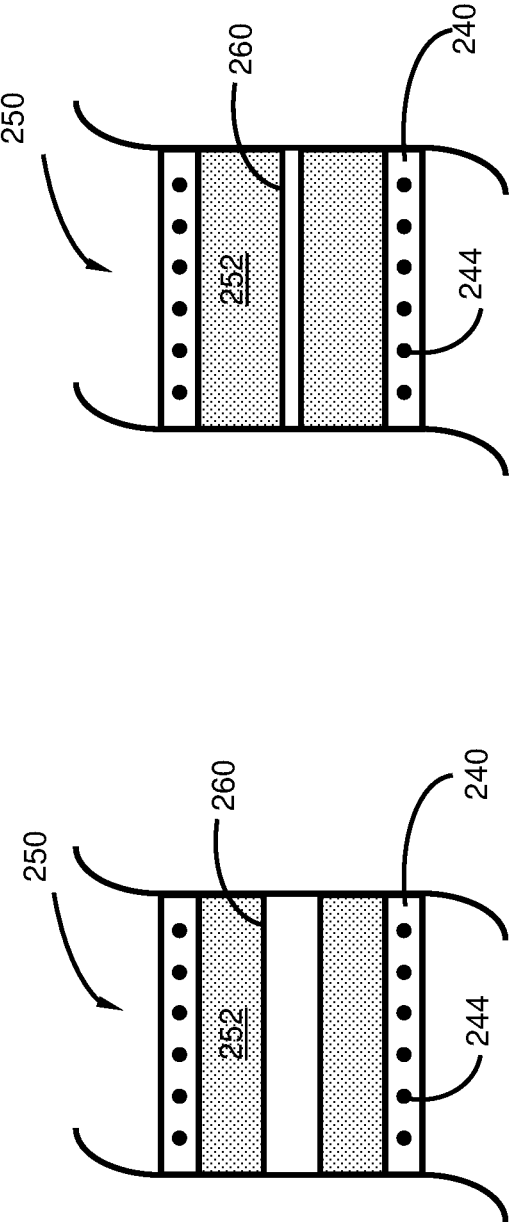
FIG. 4A:
FIG. 4B:
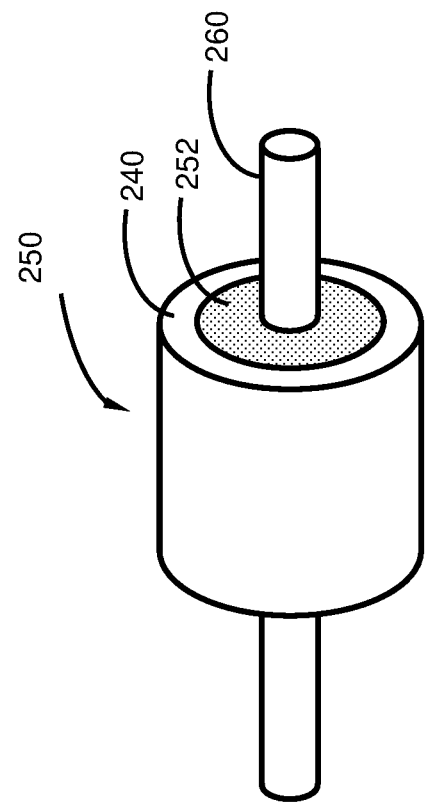
FIG. 4C:

HEATING ELEMENTS FOR THERMALLY-DRIVEN PHASE TRANSITION IMPLANTABLE MICROPUMP

BACKGROUND

Field

The present application relates generally to implantable devices configured to provide a liquid treatment substance internally to the recipient, and more specifically, heating elements of a thermally-driven device for controlling a flow of the liquid treatment substance.

Description of the Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain. Auditory prostheses of various types are widely used to improve the lives of users. Such devices include, for example, hearing aids, cochlear implants, bone conduction implants, middle ear implants, and electro-acoustic devices.

Individuals who suffer from conductive hearing loss typically have some form of residual hearing because the hair cells in the cochlea are undamaged. As a result, individuals suffering from conductive hearing loss might receive an auditory prosthesis that generates mechanical motion of the cochlea fluid instead of a hearing aid based on the type of conductive loss, amount of hearing loss and customer preference. Such prostheses include, for example, bone conduction devices and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

Forms of these auditory prostheses which are "mostly implantable," "fully implantable," or "totally implantable" have the advantage of allowing the user to have a superior aesthetic result, as the recipient is visually indistinguishable in day-to-day activities from individuals that have not received such devices. Such devices also have a further advantage in generally being inherently waterproof, allowing the recipient to shower, swim, and so forth without needing to take any special measures. Examples of such devices include, but are not limited to, totally implanted cochlear implants ("TICIs"), mostly implantable cochlear implants ("MICI"), and fully implantable middle ear implants utilizing totally implantable actuators ("TIAs").

While conventional auditory prostheses use externally disposed microphone assemblies, certain mostly, fully, or totally implantable auditory prostheses use subcutaneously implantable microphone assemblies. Such microphone assemblies are configured to be positioned (e.g., in a surgical procedure) beneath the skin and on, within, or proximate to the recipient's skull and at a location that facilitates the receipt of acoustic signals by the microphone assembly once implanted (e.g., at a location between the recipient's skin and skull, rearward and upward of the recipient's ear or in the mastoid region).

SUMMARY

In one aspect disclosed herein, an apparatus is provided which comprises an enclosure containing a hermetically sealed region, the enclosure configured to be implanted on or within a recipient. The apparatus further comprises circuitry within the hermetically sealed region, the circuitry configured to generate signals. The apparatus further comprises at least one heating element configured to receive the signals and to generate heat in response to the signals. The apparatus further comprises at least one flow control element outside the hermetically sealed region, the at least one flow control element configured to respond to the heat by controlling a flow of liquid through at least one cannula.

In another aspect disclosed herein, a method is provided which comprises selectively transmitting signals from within a hermetically sealed region to outside the hermetically sealed region. The method further comprises, in response to the signals, controllably adjusting flow of a treatment liquid through at least one cannula. The hermetically sealed region and the at least one cannula are configured to be implanted on or within a recipient.

In still another aspect disclosed herein, an auditory prosthesis is provided which comprises a biocompatible housing configured to be implanted on or within a recipient. The auditory prosthesis further comprises circuitry within a hermetically sealed region of the housing. The auditory prosthesis further comprises at least one flow controller at least partially outside the hermetically sealed region, the at least one flow controller configured to respond to signals from the circuitry by controllably administering a treatment liquid internally to the recipient.

BRIEF DESCRIPTION OF THE DRAWINGS

Embodiments are described herein in conjunction with the accompanying drawings, in which:

FIGS. 4A and 4B schematically illustrate cross-sectional views of another example flow control element in accordance with certain embodiments described herein;

FIG. 4C schematically illustrates a perspective view of the example flow control element of FIGS. 4A and 4B;

DETAILED DESCRIPTION

Figure 1:
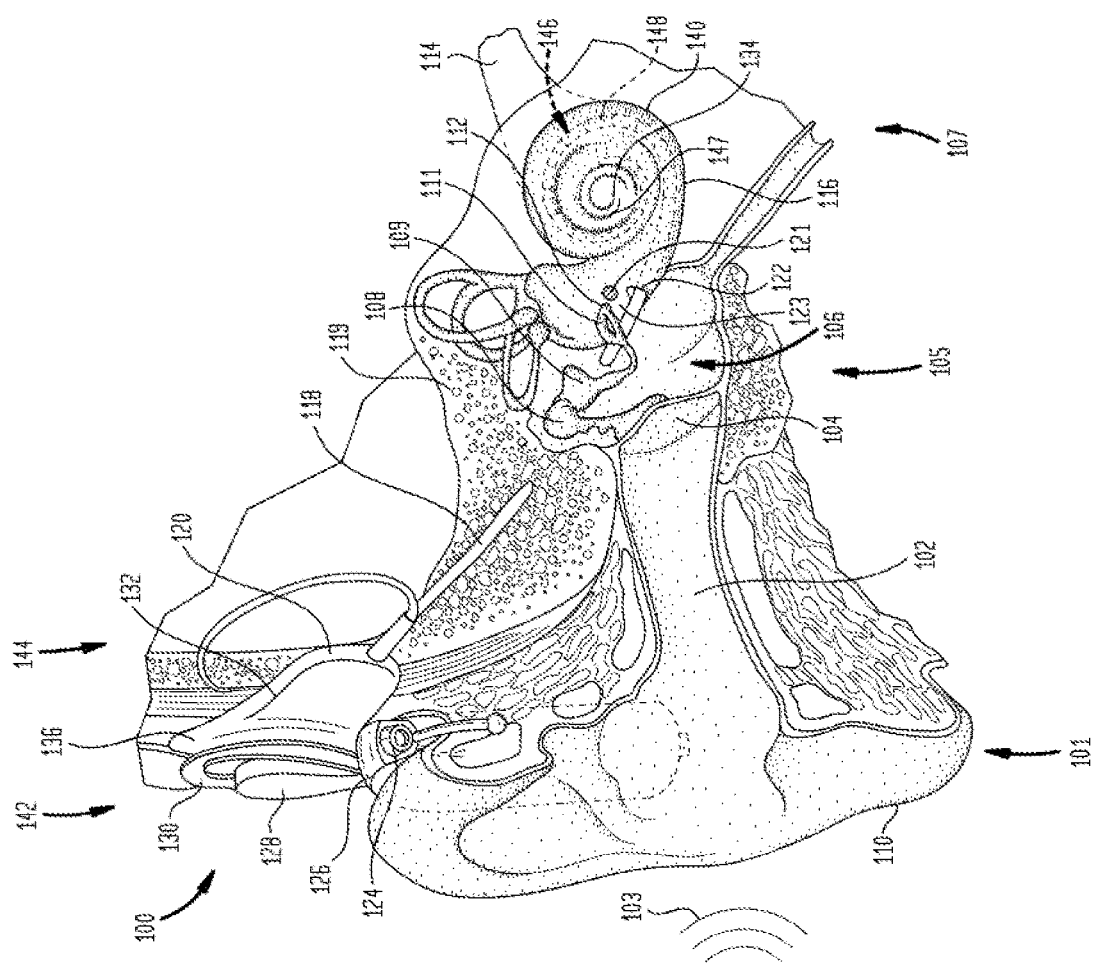
FIG. 1 is a perspective view of an example cochlear implant auditory prosthesis implanted in a recipient in accordance with certain embodiments described herein.

In the treatment of various maladies, it can be advantageous to have an extended and controllable delivery solution for use in the delivery of treatment substances (e.g., medicine; drugs) to a target location of a recipient. In general, extended treatment substance delivery refers to the delivery of treatment substances over a period of time (e.g., continuously, periodically, etc.) and can be achieved using an implantable device which controllably provides the treatment substance to the recipient. The extended delivery can be activated during or after surgery and can be extended as long as is needed. Certain embodiments described herein include features that facilitate controlled extended delivery of treatment substances. For example, certain embodiments are directed to apparatuses, systems, and methods for controlling delivery of treatment substances to a target location with a selected flow rate utilizing heating elements which controllably provide heat to one or more thermally-driven flow control elements (e.g., peristaltic pumps; valves). Certain such embodiments advantageously use circuitry within a hermetically-sealed region of an implantable delivery apparatus to provide the heat to the one or more thermally-driven flow control elements outside the hermetically-sealed region (e.g., in a non-hermetic cavity of the implantable delivery apparatus).

The teachings detailed herein are applicable, in at least some embodiments, to any type of auditory prosthesis utilizing an implantable actuator assembly including but not limited to: electro-acoustic electrical/acoustic systems, cochlear implant devices, implantable hearing aid devices, middle ear implant devices, bone conduction devices (e.g., active bone conduction devices; passive bone conduction devices, percutaneous bone conduction devices; transcutaneous bone conduction devices), Direct Acoustic Cochlear Implant (DACI), middle ear transducer (MET), electro-acoustic implant devices, other types of auditory prosthesis devices, and/or combinations or variations thereof, or any other suitable hearing prosthesis system with or without one or more external components. Embodiments can include any type of auditory prosthesis that can utilize the teachings detailed herein and/or variations thereof. An implantable, reliable, long-term drug delivery device for the vestibular system and inner ear, examples of which are described herein, are advantageously configured to be used to treat a variety of disorders, including but not limited to, chronic or recurring middle ear infections or otitis media (e.g, by administering corticosteroids either regularly in a preventative approach or whenever symptoms arise), progressive age-related hearing loss, noise-induced hearing loss, vertigo, tinnitus, and Meniere's disease. In certain embodiments, the teachings detailed herein and/or variations thereof can be utilized in other types of prostheses other than auditory prostheses or as a stand-alone device, in configurations which benefit from long-term reliability (e.g., treatment of chronic pain) by having all electronic components inside a hermetic enclosure thereby avoiding corrosion failure over a life time of the device).

FIG. 1 is a perspective view of an example cochlear implant auditory prosthesis 100 implanted in a recipient in accordance with certain embodiments described herein. The example auditory prosthesis 100 is shown in FIG. 1 as comprising an implanted stimulator unit 120 (e.g., an actuator) and an external microphone assembly 124 (e.g., a partially implantable cochlear implant). An example auditory prosthesis 100 (e.g., a totally implantable cochlear implant; a mostly implantable cochlear implant) in accordance with certain embodiments described herein can replace the external microphone assembly 124 shown in FIG. 1 with a subcutaneously implantable assembly comprising an acoustic transducer (e.g., microphone).

As shown in FIG. 1, the recipient has an outer ear 101, a middle ear 105, and an inner ear 107. In a fully functional ear, the outer ear 101 comprises an auricle 110 and an ear canal 102. An acoustic pressure or sound wave 103 is collected by the auricle 110 and is channeled into and through the ear canal 102. Disposed across the distal end of the ear canal 102 is a tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109, and the stapes 111. The bones 108, 109, and 111 of the middle ear 105 serve to filter and amplify the sound wave 103, causing the oval window 112 to articulate, or vibrate in response to vibration of the tympanic membrane 104. This vibration sets up waves of fluid motion of the perilymph within cochlea 140. Such fluid motion, in turn, activates tiny hair cells (not shown) inside the cochlea 140. Activation of the hair cells causes appropriate nerve impulses to be generated and transferred through the spiral ganglion cells (not shown) and auditory nerve 114 to the brain (also not shown) where they are perceived as sound.

As shown in FIG. 1, the example auditory prosthesis 100 comprises one or more components which are temporarily or permanently implanted in the recipient. The example auditory prosthesis 100 is shown in FIG. 1 with an external component 142 which is directly or indirectly attached to the recipient's body, and an internal component 144 which is temporarily or permanently implanted in the recipient (e.g., positioned in a recess of the temporal bone adjacent auricle 110 of the recipient). The external component 142 typically comprises one or more sound input elements (e.g., an external microphone 124) for detecting sound, a sound processing unit 126 (e.g., disposed in a Behind-The-Ear unit), a power source (not shown), and an external transmitter unit 128. In the illustrative embodiments of FIG. 1, the external transmitter unit 128 comprises an external coil 130 (e.g., a wire antenna coil comprising multiple turns of electrically insulated single-strand or multi-strand platinum or gold wire) and, preferably, a magnet (not shown) secured directly or indirectly to the external coil 130. The external coil 130 of the external transmitter unit 128 is part of an inductive radio frequency (RF) communication link with the internal component 144. The sound processing unit 126 processes the output of the microphone 124 that is positioned externally to the recipient's body, in the depicted embodiment, by the recipient's auricle 110. The sound processing unit 126 generates encoded signals, sometimes referred to herein as encoded data signals, which are provided to the external transmitter unit 128 (e.g., via a cable). As will be appreciated, the sound processing unit 126 can utilize digital processing techniques to provide frequency shaping, amplification, compression, and other signal conditioning, including conditioning based on recipient-specific fitting parameters.

The power source of the external component 142 is configured to provide power to the auditory prosthesis 100, where the auditory prosthesis 100 includes a battery (e.g., located in the internal component 144, or disposed in a separate implanted location) that is recharged by the power provided from the external component 142 (e.g., via a transcutaneous energy transfer link). The transcutaneous energy transfer link is used to transfer power and/or data to the internal component 144 of the auditory prosthesis 100. Various types of energy transfer, such as infrared (IR), electromagnetic, capacitive, and inductive transfer, may be used to transfer the power and/or data from the external component 142 to the internal component 144. During operation of the auditory prosthesis 100, the power stored by the rechargeable battery is distributed to the various other implanted components as needed.

The internal component 144 comprises an internal receiver unit 132, a stimulator unit 120, and an elongate electrode assembly 118. In some embodiments, the internal receiver unit 132 and the stimulator unit 120 are hermetically sealed within a biocompatible housing. The internal receiver unit 132 comprises an internal coil 136 (e.g., a wire antenna coil comprising multiple turns of electrically insulated single-strand or multi-strand platinum or gold wire), and preferably, a magnet (also not shown) fixed relative to the internal coil 136. The internal receiver unit 132 and the stimulator unit 120 are hermetically sealed within a biocompatible housing, sometimes collectively referred to as a stimulator/receiver unit. The internal coil 136 receives power and/or data signals from the external coil 130 via a transcutaneous energy transfer link (e.g., an inductive RF link). The stimulator unit 120 generates electrical stimulation signals based on the data signals, and the stimulation signals are delivered to the recipient via the elongate electrode assembly 118.

The elongate electrode assembly 118 has a proximal end connected to the stimulator unit 120, and a distal end implanted in the cochlea 140. The electrode assembly 118 extends from the stimulator unit 120 to the cochlea 140 through the mastoid bone 119. In some embodiments, the electrode assembly 118 may be implanted at least in the basal region 116, and sometimes further. For example, the electrode assembly 118 may extend towards apical end of cochlea 140, referred to as cochlea apex 134. In certain circumstances, the electrode assembly 118 may be inserted into the cochlea 140 via a cochleostomy 122. In other circumstances, a cochleostomy may be formed through the round window 121, the oval window 112, the promontory 123, or through an apical turn 147 of the cochlea 140.

The elongate electrode assembly 118 comprises a longitudinally aligned and distally extending array 146 of electrodes or contacts 148, sometimes referred to as electrode or contact array 146 herein, disposed along a length thereof. Although the electrode array 146 can be disposed on the electrode assembly 118, in most practical applications, the electrode array 146 is integrated into the electrode assembly 118 (e.g., the electrode array 146 is disposed in the electrode assembly 118). As noted, the stimulator unit 120 generates stimulation signals which are applied by the electrodes 148 to the cochlea 140, thereby stimulating the auditory nerve 114.

While FIG. 1 schematically illustrates an auditory prosthesis 100 utilizing an external component 142 comprising an external microphone 124, an external sound processing unit 126, and an external power source, in certain other embodiments, one or more of the microphone 124, sound processing unit 126, and power source are implantable on or within the recipient (e.g., within the internal component 144). For example, the auditory prosthesis 100 can have each of the microphone 124, sound processing unit 126, and power source implantable on or within the recipient (e.g., encapsulated within a biocompatible assembly located subcutaneously), and can be referred to as a totally implantable cochlear implant ("TICI"). For another example, the auditory prosthesis 100 can have most components of the cochlear implant (e.g., excluding the microphone, which can be an in-the-ear-canal microphone) implantable on or within the recipient, and can be referred to as a mostly implantable cochlear implant ("MICI").

Figure 2A:
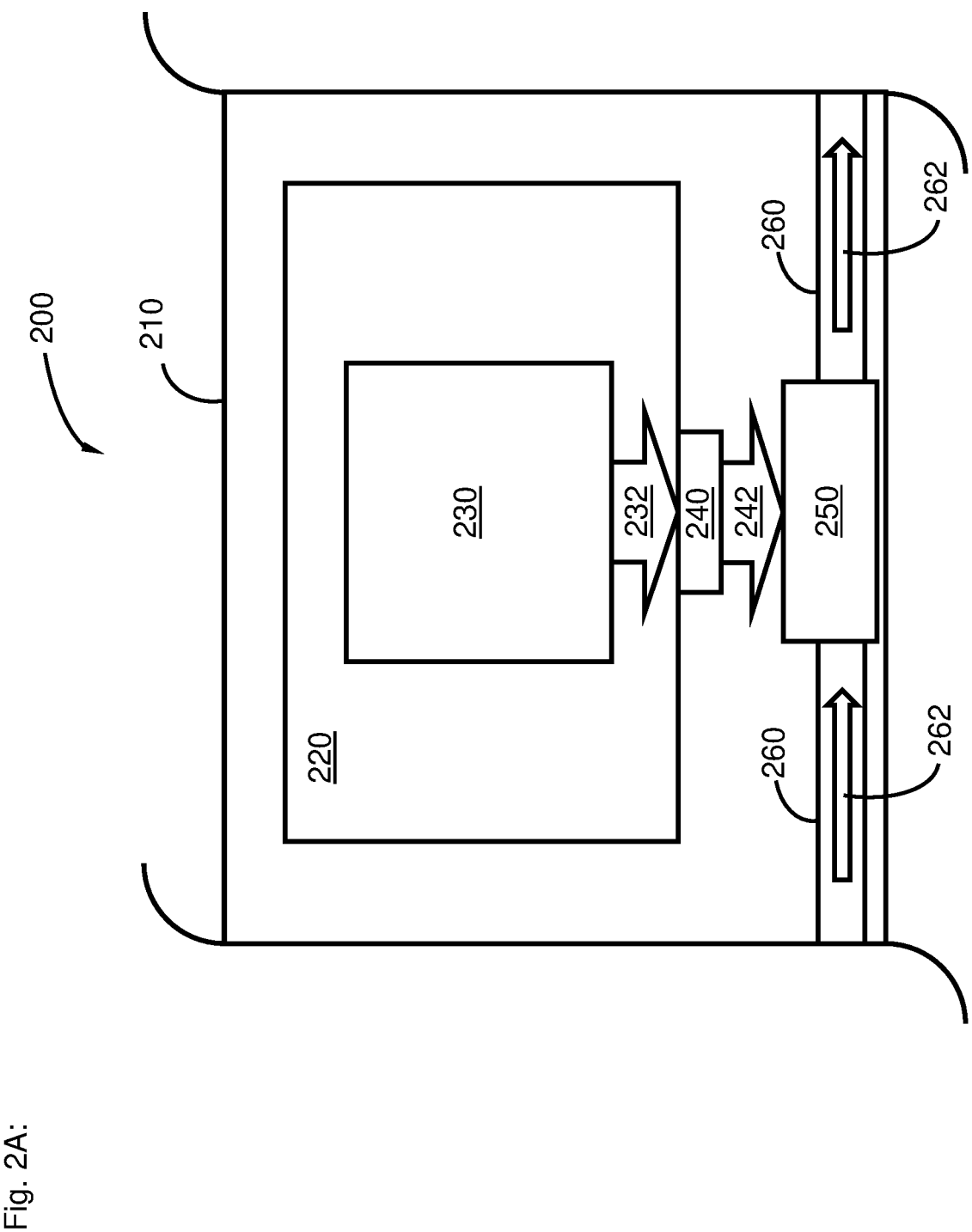
FIGS. 2A and 2B schematically illustrate portions of two example apparatus in accordance with certain embodiments described herein.
Figure 2B:
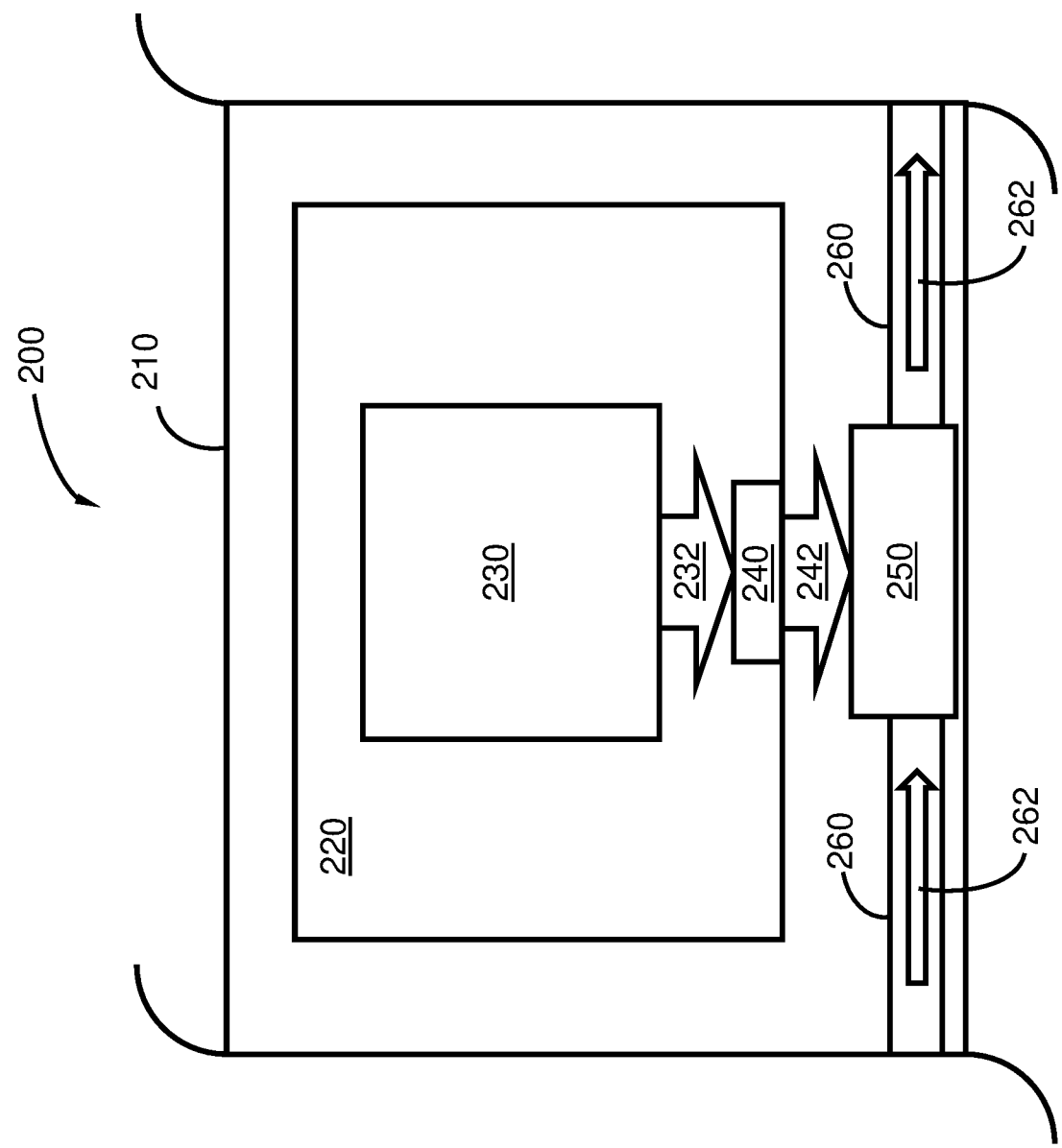

FIGS. 2A and 2B schematically illustrate portions of two example apparatus 200 in accordance with certain embodiments described herein. The apparatus 200 comprises an enclosure 210 containing a hermetically sealed region 220, the enclosure 210 is configured to be implanted on or within a recipient. The apparatus 200 further comprises circuitry 230 within the hermetically sealed region 220. The circuitry 230 is configured to generate signals 232. The apparatus 200 further comprises at least one heating element 240 configured to receive the signals 232 and to generate heat 242 in response to the signals 232. The apparatus 200 further comprises at least one flow control element 250 outside the hermetically sealed region 220. The at least one flow control element 250 is configured to respond to the heat 242 by controlling a flow of liquid 262 through at least one cannula 260. In certain embodiments, the liquid 262 comprises at least one medicament and the flow of the liquid 262 through the at least one cannula 260 comprises controlled administration of the at least one medicament internally to the recipient. In certain other embodiments, the liquid 262 comprises a body liquid from the recipient and the flow of the liquid 262 through the at least one cannula 260 comprises controlled sampling of the body liquid internally from the recipient.

As schematically illustrated by FIG. 2A, in certain embodiments, the at least one heating element 240 is outside the hermetically sealed region 220. For example, as described more fully below, the at least one heating element 240 can be affixed on an outside surface of a wall portion separating the hermetically sealed region 220 from a non-hermetically sealed region containing the at least one flow control element 250 or the at least one heating element 240 can extend outwardly from the outer surface of the wall portion into the non-hermetically sealed region. As schematically illustrated by FIG. 2B, in certain embodiments, the at least one heating element 240 is not in the non-hermetically sealed region. For example, as described more fully below, the at least one heating element 240 can be embedded within a wall portion separating the hermetically sealed region 220 from a non-hermetically sealed region containing the at least one flow control element 250 or the at least one heating element 240 can be fully within a portion of the hermetically sealed region 220 bounded at least in part by an inner surface of the wall portion. In certain such embodiments, the heat 242 from the at least one heating element 240 flows through the wall portion between the at least one heating element 240 and the at least one flow control element 250.

Figure 3A:
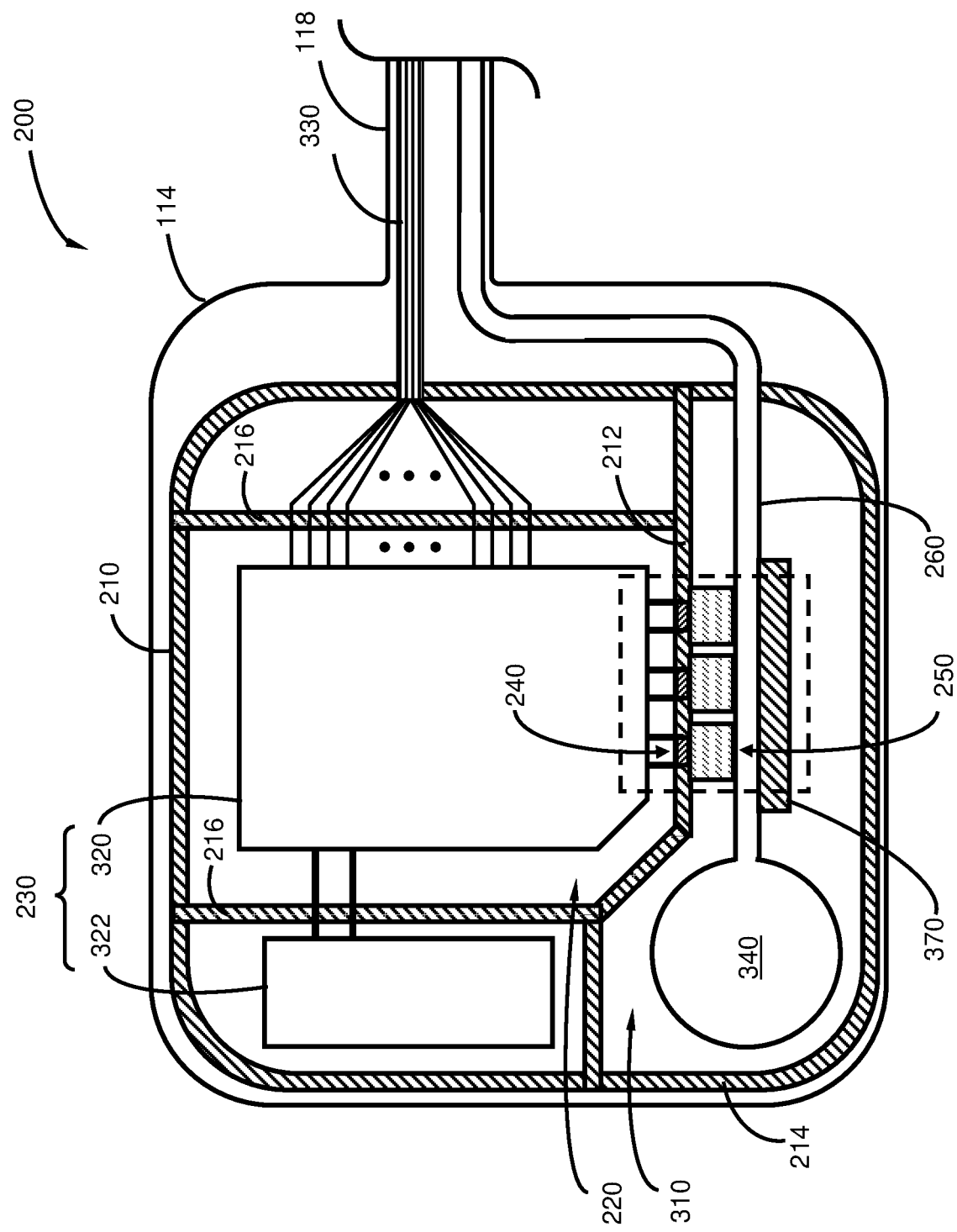
FIGS. 3A and 3B schematically illustrate another example apparatus in accordance with certain embodiments described herein.
Figure 3B:
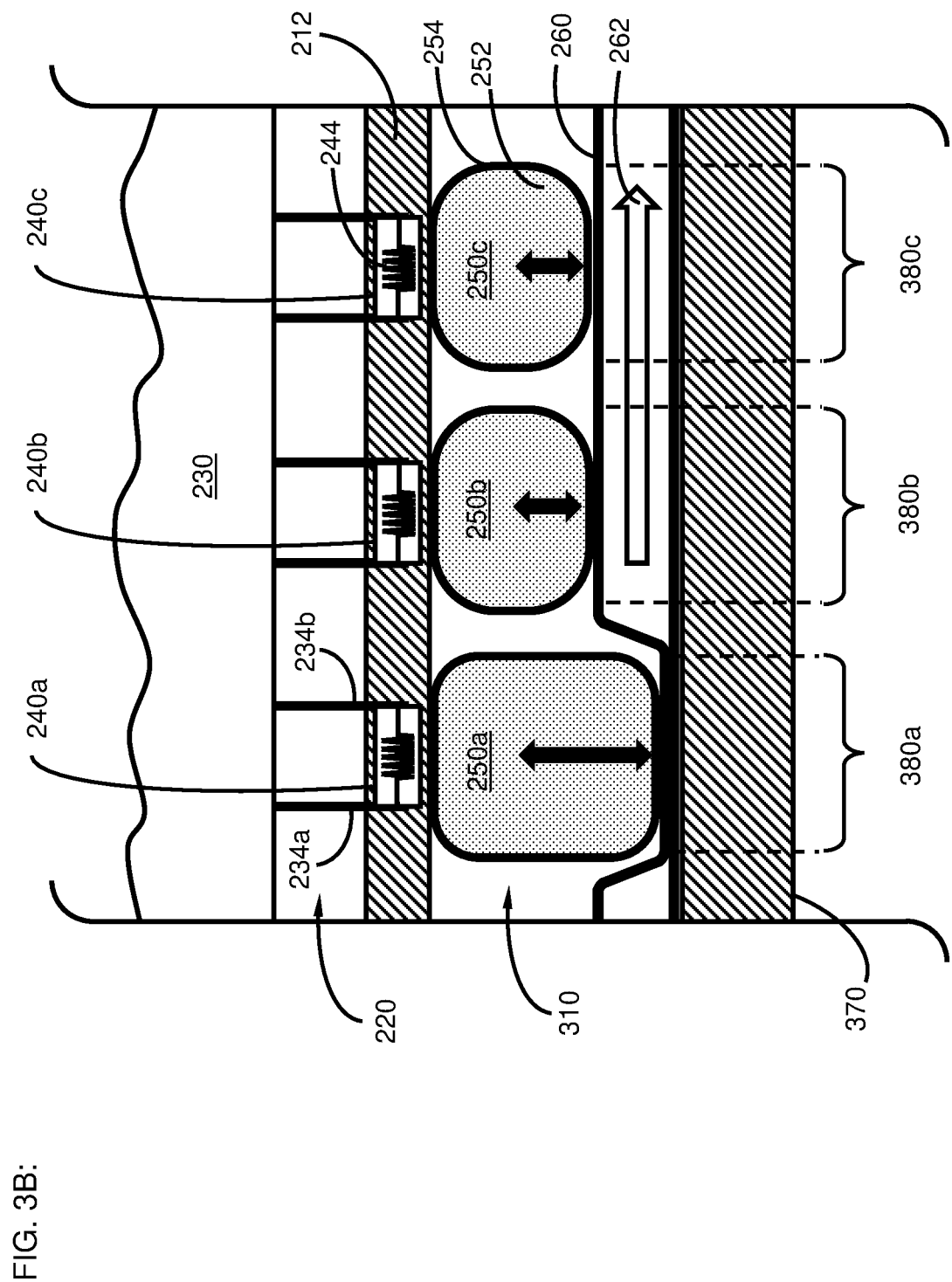

FIGS. 3A and 3B schematically illustrate another example apparatus 200 in accordance with certain embodiments described herein. The example apparatus 200 of FIGS. 3A and 3B comprises a treatment substance (e.g., liquid) delivery system that is integrated with an internal component 144 (e.g., comprising an elongate electrode assembly 118 and a stimulator unit 120) of a cochlear implant auditory prosthesis 100 and is configured to administer at least one treatment substance (e.g., fluid) to the inner ear 107 of the recipient (e.g., to the cochlea 140 via the round window 121). In certain other embodiments, the treatment substance delivery system of the example apparatus 200 is configured to administer at least one treatment substance to other portions of the recipient's body (e.g., bones; spine; organs; heart; lungs; eyes; liver; brain; stomach; pancreas; kidneys), either separately from any other implantable device or as an integrated part of another implantable device configured to provide other benefits or functionalities to the recipient.

The enclosure 210 (e.g., housing) of certain embodiments bounds the hermetically sealed region 220 and comprises a biocompatible material (e.g., biocompatible metal; titanium; grade 5 titanium; ceramics; glass; polymers). For example, as schematically illustrated in FIG. 3A, one or more walls 212 of the enclosure 210 bound portions of the hermetically sealed region 220 and seal these portions from substances in the environment in which the apparatus 200 is implanted and/or in one or more non-hermetically sealed regions (e.g., separated from the environment in which the apparatus 200 is implanted by one or more walls 214 of the enclosure 210). In certain embodiments, the enclosure 210 further comprises one or more walls 216 separating portions of the hermetically sealed region 220 from one another.

As schematically illustrated by FIG. 3A, the circuitry 230 within the hermetically-sealed region 220 comprises at least one printed-circuit board assembly 320 (e.g., comprising a microprocessor) and at least one power supply 322 (e.g., battery; RF power transfer coil). In certain embodiments, the circuitry 230 is configured to control the treatment substance delivery system of the example apparatus 200. For example, the circuitry 230 of FIG. 3A is in electrical communication with the at least one heating element 240 and is configured to selectively transmit the signals 232 (e.g., electrical current) to the at least one heating element 240 which selectively generates heat 242 in response to the signals 232. In certain embodiments, the circuitry 230 is further configured to provide another functionality of the apparatus 200. For example, the circuitry 230 of FIG. 3A is configured to control the cochlear implant auditory prosthesis 100 and is in electrical communication with a plurality of electrical conduits 330 which extend along the elongate electrode assembly 118 into the cochlea 140 to the electrodes 148 (not shown in FIG. 3A) of the cochlear implant auditory prosthesis 100.

As schematically illustrated by FIG. 3A, the one or more non-hermetically sealed regions comprise at least one non-hermetic cavity 310 (e.g., bounded at least partially by the enclosure 210) containing the at least one flow control element 250 and at least a portion of the at least one cannula 260. The at least one cannula 260 (e.g., fluid conduit; fluid channel; tube; pipe; hose; duct) is configured to deliver at least one treatment substance (e.g., liquid 262) internally to the recipient, with the flow of the at least one treatment substance controlled by the at least one flow control element 250. For example, as schematically illustrated by FIG. 3A, the at least one cannula 260 can extend from the non-hermetic cavity 310 of the enclosure 210 through the elongate electrode assembly 118 of a cochlear implant auditory prosthesis 100. The at least one cannula 260 can extend into the inner ear 107 of the recipient and can have an outlet port (not shown in FIG. 3A) at the round window 121 or in the cochlea 140.

In certain embodiments, the at least one non-hermetic cavity 310 further comprises at least one reservoir 340, with the at least one cannula 260 in fluidic communication with the at least one reservoir 340 and the recipient. In certain other embodiments, the at least one reservoir 340 is in a non-hermetically sealed region but is outside the at least one non-hermetic cavity 310 of the enclosure 210 (e.g., spaced from the enclosure 210 but in fluidic communication with a portion of the at least one cannula 260 that extends from the at least one non-hermetic cavity 310). For example, the at least one reservoir 340 can be positioned between layers of the recipient's tissue or adjacent to a subcutaneous outer surface of the recipient's skull (e.g., positioned in a surgically created pocket at the outer surface adjacent to a superior portion of the temporal bone). The at least one reservoir 340 of certain embodiments is, prior to or after implantation, at least partially filled with at least one treatment substance for delivery to the recipient. The treatment substance can be, for example, in a liquid form, a gel form, and/or comprise nanoparticles or pellets. In certain embodiments, the treatment substance can initially be in a crystalline/solid form that is subsequently dissolved. For example, the at least one reservoir 340 can include two chambers, one that comprises a fluid (e.g., artificial perilymph or saline) and one that comprises the crystalline/solid treatment substance. The fluid can be mixed with the crystalline/solid treatment substance to form a fluid or gel treatment substance that can be subsequently delivered to the recipient.

In certain embodiments, the at least one reservoir 340 includes a needle port so that the at least one reservoir 340 can be refilled via a needle injection through the skin. In certain other embodiments, the at least one reservoir 340 is explanted and replaced with another reservoir that is, prior to or after implantation, at least partially filled with a treatment substance. In certain embodiments, the at least one reservoir 340 has a preformed shape and is implanted in this shape. In certain other embodiments, the at least one reservoir 340 has a first shape that facilitates implantation and a second shape for use in delivering treatment substances to the recipient. For example, the at least one reservoir 340 can have a rolled or substantially flat initial shape that facilitates implantation, and the at least one reservoir 340 can be configured to then expand after implantation. Certain such embodiments can be used, for example, to insert the at least one reservoir 340 through a tympanostomy into the middle ear 105 or the ear canal 102, through an opening in the inner ear 107, or to facilitate other minimally invasive insertions.

FIG. 3B schematically illustrates a portion of the example apparatus 200 of FIG. 3A (denoted in FIG. 3A by a dashed line) in accordance with certain embodiments described herein. In certain embodiments, as schematically illustrated in FIG. 3B, the apparatus 200 comprises a plurality of heating elements 240 configured to generate heat 242 in response to signals 232 received from the circuitry 230. For example, each heating element 240 can comprise at least one electrical resistor 244 and the circuitry 230 can comprise a plurality of electrical conduits 234a, 234b arranged in pairs, each pair in electrical communication with a corresponding heating element 240. For each heating element 240, signals 232 (e.g., electrical current) flow from the printed-circuit board assembly 320, through a first electrical conduit 234a, through the at least one electrical resistor 242, and back to the printed-circuit board assembly 320 through the second electrical conduit 234b. In certain other embodiments, two or more of the heating elements 240 share a common electrical conduit 234 and the circuitry 230 is configured to selectively route the signals 232 (e.g., driving electrical current) among the electrical conduits 234 to the appropriate heating element 240.

In certain embodiments, as schematically illustrated by FIG. 3B, the apparatus 200 further comprises a plurality of flow control elements 250 arranged along the cannula 260, each flow control element 250 in mechanical communication with a corresponding portion of the cannula 260. FIG. 3B shows the plurality of heating elements 240 and the plurality of flow control elements 250 corresponding to one another in a one-to-one configuration (e.g., each heating element 240 provides heat to one corresponding flow control element 250 and each flow control element 250 receives heat from one corresponding heating element 240). In certain other embodiments, two or more heating elements 240 correspond to each flow control element 250 (e.g., multiple heating elements 240 provide heat to one corresponding flow control element 250), at least some of the heating elements 240 correspond to two or more flow control elements 250 (e.g., at least some of the heating elements 240 each provides heat to two or more flow control elements 250), and/or at least some of the flow control elements 250 correspond to two or more heating elements 240 (e.g., at least some of the flow control elements 250 receive heat from two or more heating elements 240).

In certain embodiments, the plurality of flow control elements 250 are configured to receive the heat 242 from the plurality of heating elements 240 and to reversibly change size in response to the heat 242. For example, the flow control element 250 can expand in response to the heat 242 and can contract in response to absence of the heat 242. In another example, the flow control element 250 can expand in response to absence of the heat 242 and can contract in response to the heat 242. In certain embodiments, the size of the flow control element 250 in the expanded state can be in a range of at least 3%, in a range of 3% to 30%, or in a range of 5% to 15% greater than the size of the flow control element 250 in the non-expanded or contracted state.

In certain embodiments, each of the flow control elements 250 comprises a phase-change material 252 within a resiliently flexible container 254 (e.g., comprising a biocompatible polymer), the phase-change material 252 configured to respond to the heat from the heating elements 250 by changing from a first (e.g., non-expanded) phase having a size (e.g., length; width; perimeter; area; volume) with a first magnitude to a second (e.g., expanded) phase having a size with a second magnitude different from (e.g., larger than) the first magnitude. The phase-change material 252 of certain embodiments is configured to transition between the first phase and the second phase (e.g., between a liquid phase and a gas phase; between a solid phase and a liquid phase) repeatedly, reversibly, and without hysteresis. Examples of phase-change materials 252 compatible with certain embodiments described herein include, but are not limited to: wax; paraffin; gallium; gallium-iridium alloy. In certain embodiments, the at least one flow control element 250 is configured to allow flow of the liquid 262 through a corresponding portion of the at least one cannula 260 when the phase-change material 252 is in the first (e.g., non-expanded) phase and is further configured to not allow flow of the liquid 262 through the corresponding portion of the at least one cannula 260 when the phase-change material 252 is in the second (e.g., expanded) phase.

In certain embodiments, the at least one cannula 260 has an outer diameter in a range of 100 microns to 500 microns and an inner diameter in a range of 50 microns to 250 microns. The at least one cannula 260 of certain embodiments comprises a resiliently flexible wall (e.g., comprising a biocompatible polymer) with a wall thickness in a range of 25 microns to 150 microns. The at least one cannula 260 is configured to be compressed by a force applied by the at least one flow control element 250 to the at least one cannula 260, and to return to its uncompressed configuration when the force applied by the at least one flow control element 250 is removed from the at least one cannula 260. In its compressed configuration, the at least one cannula 260 reduces (e.g., prevents; blocks) flow of the liquid 262 through the at least one cannula 260.

In certain embodiments, as schematically illustrated by FIG. 3B, the flow control elements 250 are between the plurality of heating elements 240 and the cannula 260 and the cannula 260 is between the flow control elements 250 and a rigid support 370 (e.g., comprising a rigid biocompatible material, such as titanium). FIG. 3B shows the flow control elements 250 all on a common side of the cannula 260 and configured to compress corresponding portions of the cannula 260 against the common rigid support 370 on an opposite side of the cannula 260. In certain other embodiments, two or more of the flow control elements 250 are on different sides of the cannula 260 than one another and are configured to compress the corresponding portions of the cannula 260 against corresponding rigid supports 370, each of which is positioned on an opposite side of the cannula 260 from the corresponding flow control element 250.

FIGS. 4A and 4B schematically illustrate cross-sectional views of another example flow control element 250 in accordance with certain embodiments described herein. FIG. 4C schematically illustrates a perspective view of the example flow control element 250 of FIGS. 4A and 4B. The flow control element 250 of FIGS. 4A-4C comprises a phase-change material 252 that is surrounded by a heating element 240, and the phase-change material 252 surrounds a corresponding portion of the cannula 260. As shown in FIG. 4A, when the flow control element 250 is in a first state, the cannula 260 has a first cross-sectional area. As shown in FIG. 4B, when the flow control element 250 is in a second state, the cannula has a second cross-sectional area smaller than the first cross-sectional area such that flow resistance of the liquid 262 is greater in the second state than in the first state. In certain embodiments, the heating element 240 comprises a cuff electrode comprising an electrical resistor 244 (e.g., a platinum wire coil) extending around the phase-change material 252 and enclosed in a heating jacket 246 (e.g., silicone) extending around the phase-change material 252. The electrical resistor 244 is in electrical communication with the circuitry 230 within the hermetically sealed region 220 (not shown in FIGS. 4A-4C) and is configured to apply resistively-generated heat to the phase-change material 252. In certain embodiments, the heating jacket 246 extends around a perimeter of the phase-change material 252, as schematically illustrated by FIG. 4C, and is configured to constrain the outer perimeter of the phase-change material 252 from expanding radially outward from the cannula 260. In certain other embodiments, the heating jacket 246 also extends over the end portions of the phase-change material 252 such that the heating jacket 246 fully encloses the phase-change material 252 around the portion of the cannula 260 and is configured to constrain the phase-change material 252 from expanding longitudinally along the cannula 260.

In certain embodiments, each flow control element 250 is configured to selectively respond to the heat 242 from the heating elements 240 by expanding and applying a force to the corresponding portion of the cannula 260, the force sufficient to resiliently compress the portion of the cannula 260 against the rigid support 370 such that the liquid 262 in the portion of the cannula 260 is displaced from the portion of the cannula 260 and further flow of the liquid 262 through the portion of the cannula 260 is reduced (e.g., prevented; blocked). For example, as schematically illustrated in FIG. 3B, a first flow control element 250a responds to the heat 242 from a first heating element 240a by increasing in size in a direction towards the rigid support 370, thereby compressing the corresponding portion of the cannula 260 between the first flow control element 250a and the rigid support 370 so as to displace the liquid 262 from the portion of the cannula 260 (e.g., towards the right in FIG. 3B) and to prevent the further flow of the liquid 262 through the corresponding portion of the cannula 260. When the first heating element 240*a* ceases providing the heat 242 to the first flow control element 250*a*, the first flow control element 250*a* contracts to its smaller size, thereby allowing the corresponding portion of the cannula 260 to elastically return to its non-compressed configuration and permitting flow of the liquid 262 into and through the corresponding portion of the cannula 260.

In certain embodiments, the other flow control elements (e.g., the second flow control element 250*b* and the third flow control element 250*c* shown in FIG. 3B) are similarly configured to selectively respond to the heat 242 from the corresponding heating elements 240 (e.g., the second heating element 240*b* and the third heating element 240*c*). In certain embodiments, each flow control element 250 is configured to be individually actuated (e.g., expanded) independently from the other flow control elements 250. For example, each flow control element 250 can be responsive only to the heat 242 from the corresponding heating element 240 (e.g., the first flow control element 250*a* is unaffected by heat generated by either the second heating element 240*b* or the third heating element 240*c*, the second flow control element 250*b* is unaffected by heat generated by either the first heating element 240*a* or the third heating element 240*c*, and the third flow control element 250*c* is unaffected by heat generated by either the first heating element 240*a* or the second heating element 240*b*). For example, the heating elements 240 can be configured in an alternating fashion on opposite sides of the cannula 260. In certain embodiments, a plurality of the example flow control elements 250 schematically illustrated by FIGS. 4A-4C are configured to be selectively and individually actuated to control the flow of liquid 262 through the cannula 260.

In certain embodiments, the flow control elements 250 are selectively and individually actuated to controllably administer a medicament internally to the recipient. In certain other embodiments, the flow control elements 250 are selectively and individually actuated to draw body liquid into the implantable device (e.g., to facilitate diagnostic measures of body liquids that may be difficult to sample otherwise). For example, perilymph liquid can be retrieved and transported (e.g., sucked) from the scala vestibule through the cannula 260 into a reservoir which is accessible through the skin. For another example, unwanted fluids can be removed from body spaces which are otherwise difficult to reach (e.g., to treat chronic pericardial effusion).

In certain embodiments, at least one flow control element 250 is configured to be used as a selectively actuated valve to controllably allow flow of the liquid 262 through the at least one cannula 260 or to controllably prevent flow of the liquid 262 through the at least one cannula 260 (e.g., to controllably provide the treatment liquid 262 to the recipient). For example, a flow control element 250 can be positioned along the at least one cannula 260 (e.g., at or near the treatment site; at or near the at least one outlet port of the at least one cannula 260). The signals 232 for actuating the flow control element 250 can be provided by the circuitry 230 within the hermetically-sealed region 220 to the flow control element 250 outside the hermetically-sealed region 220.

In certain embodiments, the individual flow control elements 250 are configured to be selectively actuated (e.g., operating as "pistons") to peristaltically pump the liquid 262 through the at least one cannula 260 (e.g., to controllably provide the treatment liquid 262 to the recipient). For example, the flow control elements 250 can be positioned along the at least one cannula 260 between the at least one reservoir 340 and the at least one outlet port of the at least one cannula 260. In certain embodiments, the flow control elements 250 are selectively (e.g., sequentially) actuated in accordance with a timing scheme that results in a pumping rate in a range of 10 nanoliters/minute to 500 nanoliters/minute.

For example, referring to FIG. 3B, the flow control elements 250 can initially each be in their non-actuated (e.g., non-expanded) state such that none of the corresponding portions of the cannula 260 are compressed. By providing heat 242 from the first heating element 240*a* to the first flow control element 250*a*, the first flow control element 250*a* is activated (e.g., expands) and compresses the corresponding portion 380*a* of the cannula 260, thereby forcing (e.g., pushing) liquid 262 that was in the corresponding portion 380*a* of the cannula 260 to move towards the right in FIG. 3B. By further providing heat 242 from the second heating element 240*b* to the second flow control element 250*b*, the second flow control element 250*b* is activated (e.g., expands) and compresses the corresponding portion 380*b* of the cannula 260, thereby forcing (e.g., pushing) the liquid 262 that was in the corresponding portion 380*b* of the cannula 260 to move towards the right in FIG. 3B. By further providing heat 242 from the third heating element 240*c* to the third flow control element 250*c*, the third flow control element 250*c* is activated (e.g., expands) and compresses the corresponding portion 380*c* of the cannula 260, thereby forcing (e.g., pushing) the liquid 262 that was in the corresponding portion 380*c* of the cannula 260 to move towards the right in FIG. 3B. By ceasing to provide heat 242 from the first heating element 240*a* to the first flow control element 250*a* and ceasing to provide heat 242 from the second heating element 240*b* to the second flow control element 250*b*, while continuing to provide heat 242 from the third heating element 240*c* to the third flow control element 250*c*, the first and second portions 380*a*, 380*b* of the cannula 260 can elastically return to their non-compressed state, thereby allowing additional liquid 262 to flow from the left in FIG. 3B (e.g., from the reservoir 340) into the first and second portions 380*a*, 380*b* of the cannula 260 to continue the process of peristaltically pumping the liquid 262 from the at least one reservoir 340 through the at least one cannula 260 to the recipient. Other schemes for selectively (e.g., sequentially) actuating the flow control elements 250 are also compatible with certain embodiments described herein.

While FIGS. 3A-3B schematically illustrate an example apparatus 200 comprising at least one flow control element 250 that is separate from but proximal to (e.g., contacting) the at least one cannula 260, in certain other embodiments, the at least one flow control element 250 is integrated with the at least one cannula 260 or comprises a portion of the at least one cannula 260. For example, the at least one flow control element 250 can comprise the liquid 262 within a portion 380 of the at least one cannula 260 corresponding to (e.g., receiving heat from) at least one heating element 240. Heat 242 from the at least one heating element 240 can cause a phase change (e.g., liquid to gas) of at least some of the liquid 262 to be delivered, creating a bubble within the portion 380 of the at least one cannula 260 (e.g., without an intermediate phase-change material). The bubble can force (e.g., push) other portions of the liquid 262 through the at least one cannula 260 to the recipient. Upon ceasing application of the heat 242, the gas generated from the phase change of the liquid 262 can compress, returning to the liquid phase to be subsequently delivered to the recipient, and the volume within the at least one cannula 260 previously filled by the gas can be filled with additional liquid 262 (e.g., from the at least one reservoir 240).

FIGS. 5A-5D schematically illustrate example heating elements 240 in accordance with certain embodiments described herein. Each example heating element 240 of FIGS. 5A-5C extends through a wall 212 of the enclosure 210, the wall 212 separating a hermetically-sealed region 220 from a non-hermetically-sealed region (e.g., a non-hermetic cavity 310 of the enclosure 210). Each example heating element 240 of FIGS. 5A-5C comprises a feedthrough 410 (e.g., ceramic; $Al_2O_3$) having a surface 420 facing the non-hermetic cavity 310. The feedthrough 410 is mechanically coupled to a metallic portion 412 (e.g., titanium grade 5) of the wall 212 by a hermetic braze joint 414 (e.g., TiCuN) between the feedthrough 410 and the metallic portion 412 of the wall 212. Each example heating element 240 of FIGS. 5A-5C further comprises a resistor 244 comprising a biocompatible metal (e.g., gold; platinum) portion 422. Each example heating element 240 of FIGS. 5A-5C further comprises two metallic portions 424a, 424b that extend at least partially through the feedthrough 410 and are hermetically bonded with the feedthrough 410 (e.g., the bond established during a sintering process). The metallic portions 424a, 424b are in electrical communication with the metal portion 422 and with corresponding electrical conduits 234a, 234b of the circuitry 230 and are configured to provide electrical current from the circuitry 230 to the resistor 244.

Figure 5A:
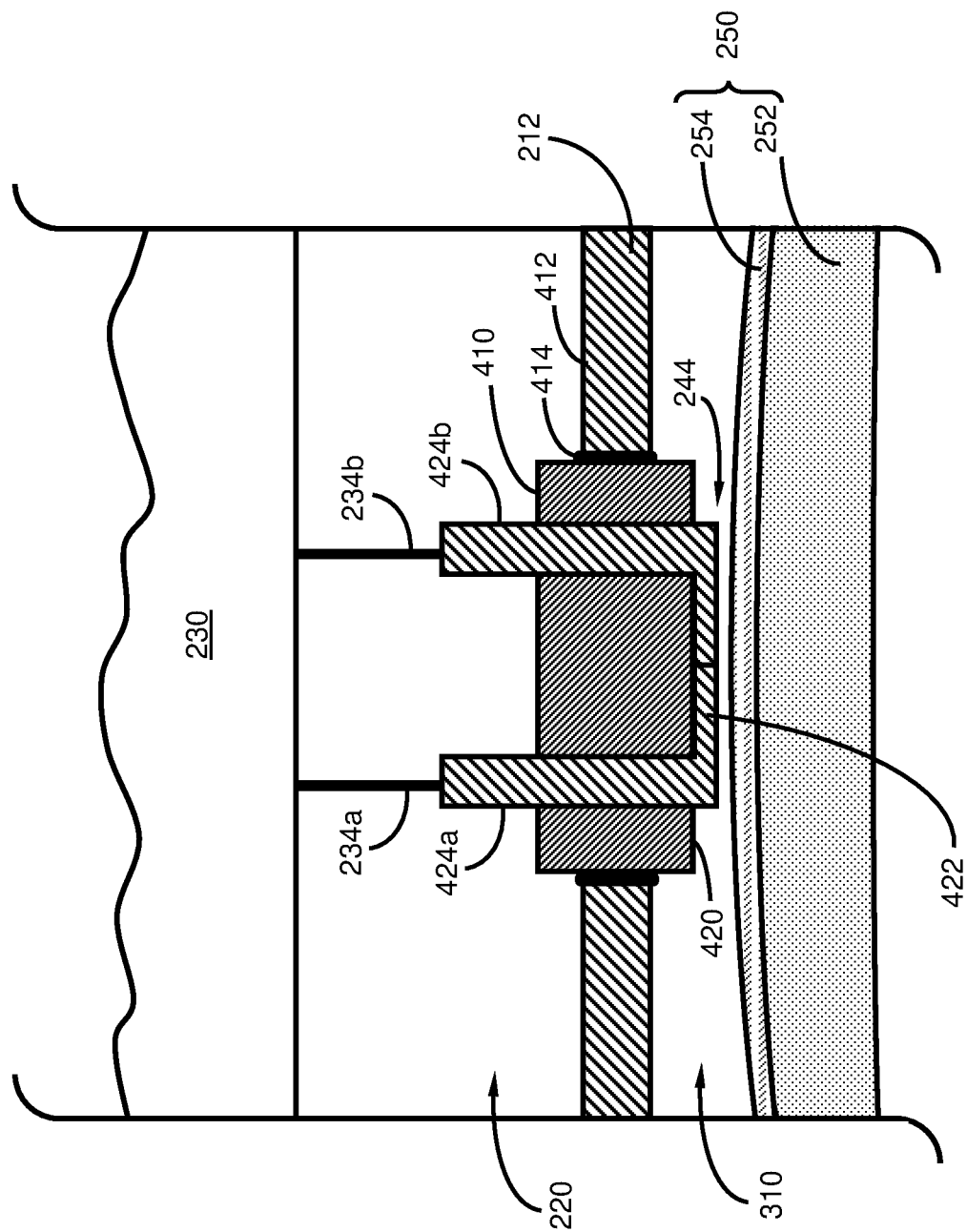
FIGS. 5A-5D schematically illustrate example heating elements in accordance with certain embodiments described herein.
Figure 5B:
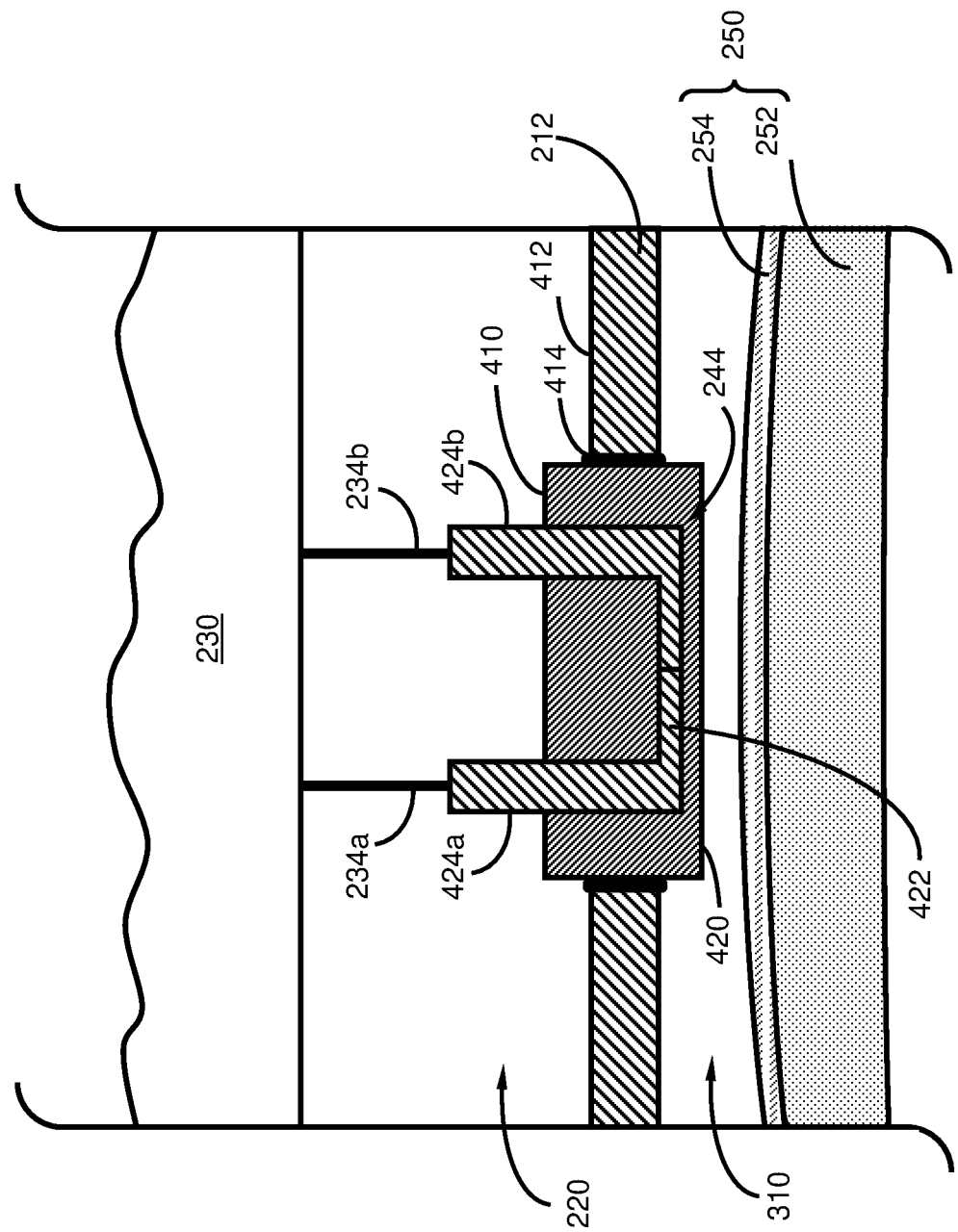
Figure 5C:
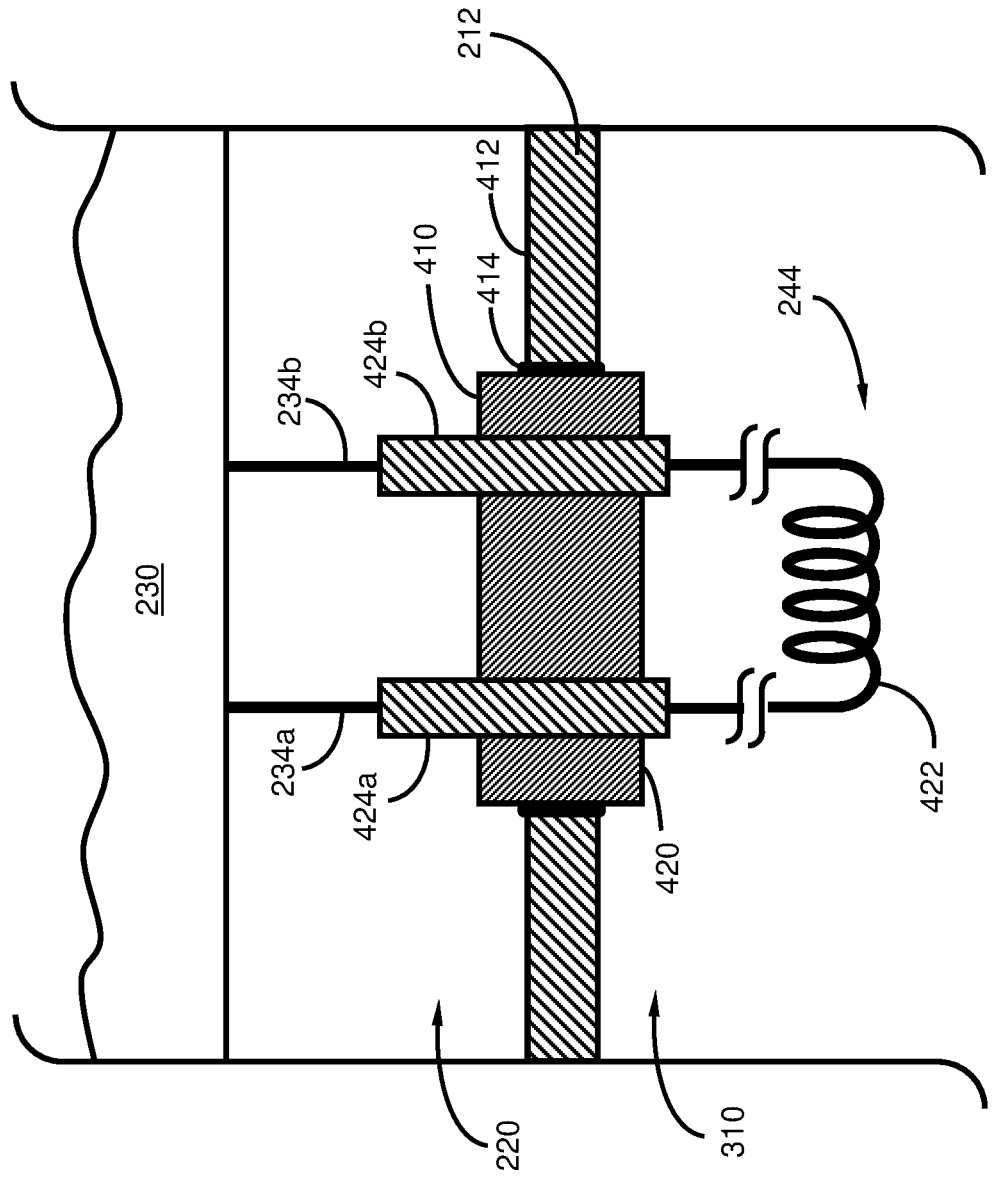

As schematically illustrated in FIG. 5A, the metal portion 422 of the resistor 244 is on the surface 420 of the feedthrough 410, is exposed to the non-hermetic cavity 310, and is proximal to the flow control element 250 (e.g., a direct heating configuration). As schematically illustrated in FIG. 5B, the metal portion 422 of FIG. 5B is fully enclosed within the feedthrough 410 which is proximal to the flow control element 250 (e.g., an indirect heating configuration). As schematically illustrated in FIG. 5C, the metal portion 422 of the resistor 244 (e.g., platinum coil) is spaced away from the feedthrough 410 (e.g., a remote heating configuration) and is proximal to the flow control element 250 (not shown in FIG. 5C). In each of FIGS. 5A-5C, the metal portion 422 is configured to generate heat in response to electrical current flowing through the metal portion 422. For example, the metal portion 422 can have an electrical conductivity and dimensions (e.g., width; thickness; length; cross-sectional area) configured to provide a predetermined amount of resistive heating in response to a predetermined amount of electrical current flowing through the metal portion 422.

Figure 5D:
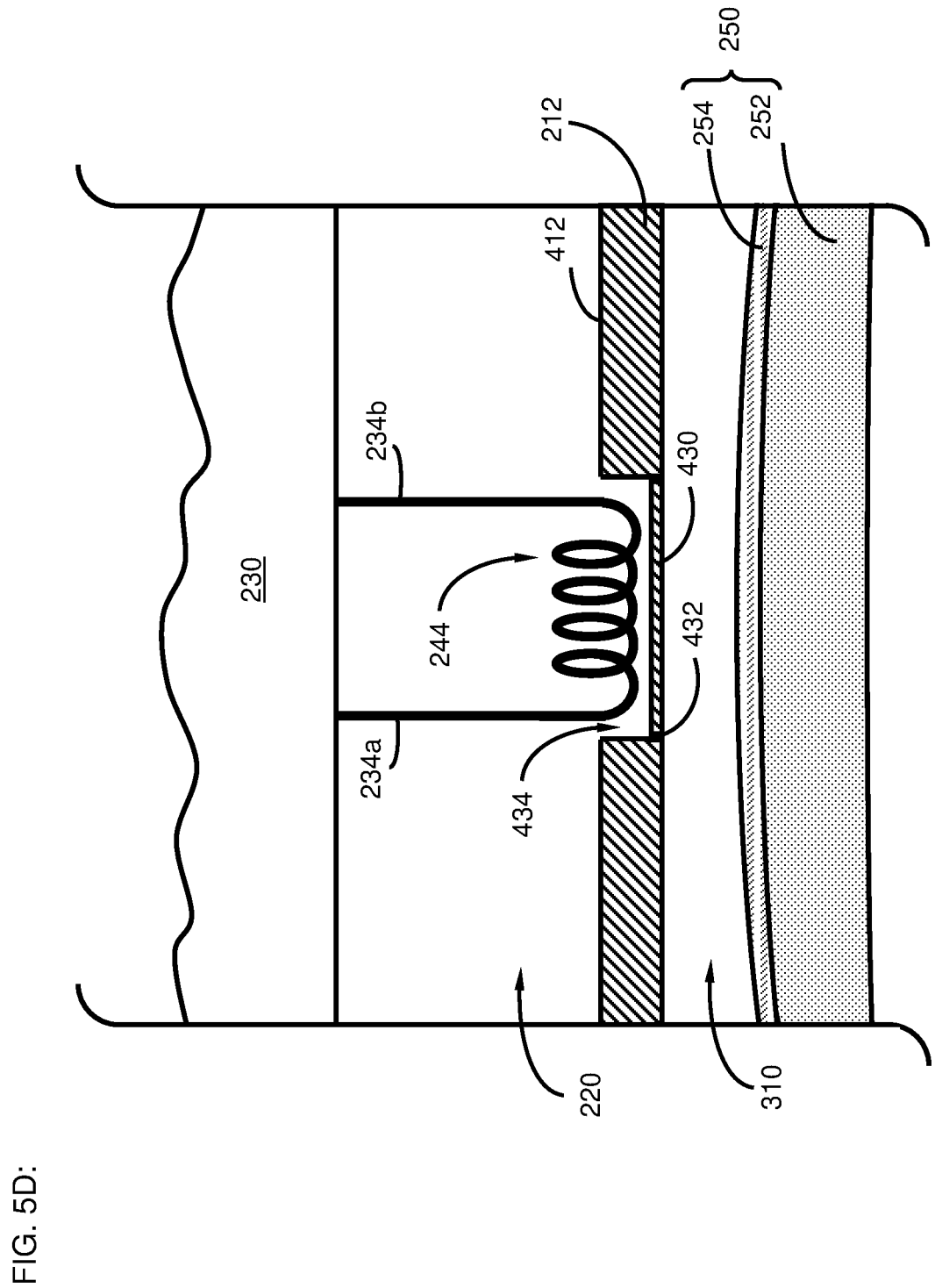

The example heating element 240 schematically illustrated by FIG. 5D does not extend through the wall 212 of the enclosure 210 separating the hermetically-sealed region 220 from the non-hermetically-sealed region (e.g., a non-hermetic cavity 310 of the enclosure 210). The resistor 244 of the example heating element 240 of FIG. 5D is positioned within the hermetically-sealed region 220 and is in electrical communication with the circuitry 230 by two electrical conduits 234a, 234b. Because the resistor 244 is within the hermetically-sealed region 220, the resistor 244 can comprise either a biocompatible material (e.g., gold; platinum) or a non-biocompatible material (e.g., tungsten). In certain embodiments, the resistor 244 comprises an electrical insulating coating (e.g., PTFE; SiC) configured to electrically isolate the resistor 244 from the wall 212.

The wall 212 of the example heating element 240 of FIG. 5D comprises a heat-transferring portion 430 configured to allow heat to propagate from the resistor 244 to the flow control element 250. In certain embodiments, the heat-transferring portion 430 comprises the same material as does the surrounding portions of the wall 212 (e.g., titanium grade 5; ceramic; glass), while in certain embodiments, the heat-transferring portion 430 comprises a different material than does the surrounding portions of the wall 212, the material of the heat-transferring portion of 430 selected to provide sufficient thermal conductivity (e.g., gold). In certain embodiments, the portion 430 is a separate lamina that is mechanically coupled (e.g., by one or more laser welds 432) to the surrounding portions of the wall 212 sealing a hole 434 through the wall 212, while in certain other embodiments, the heat-transferring portion 430 is unitary with the surrounding portions of the wall 212 (e.g., the portion 430 comprises a machined portion of the wall 212 so as to have a smaller thickness than does the surrounding portions of the wall 212).

Figure 6:
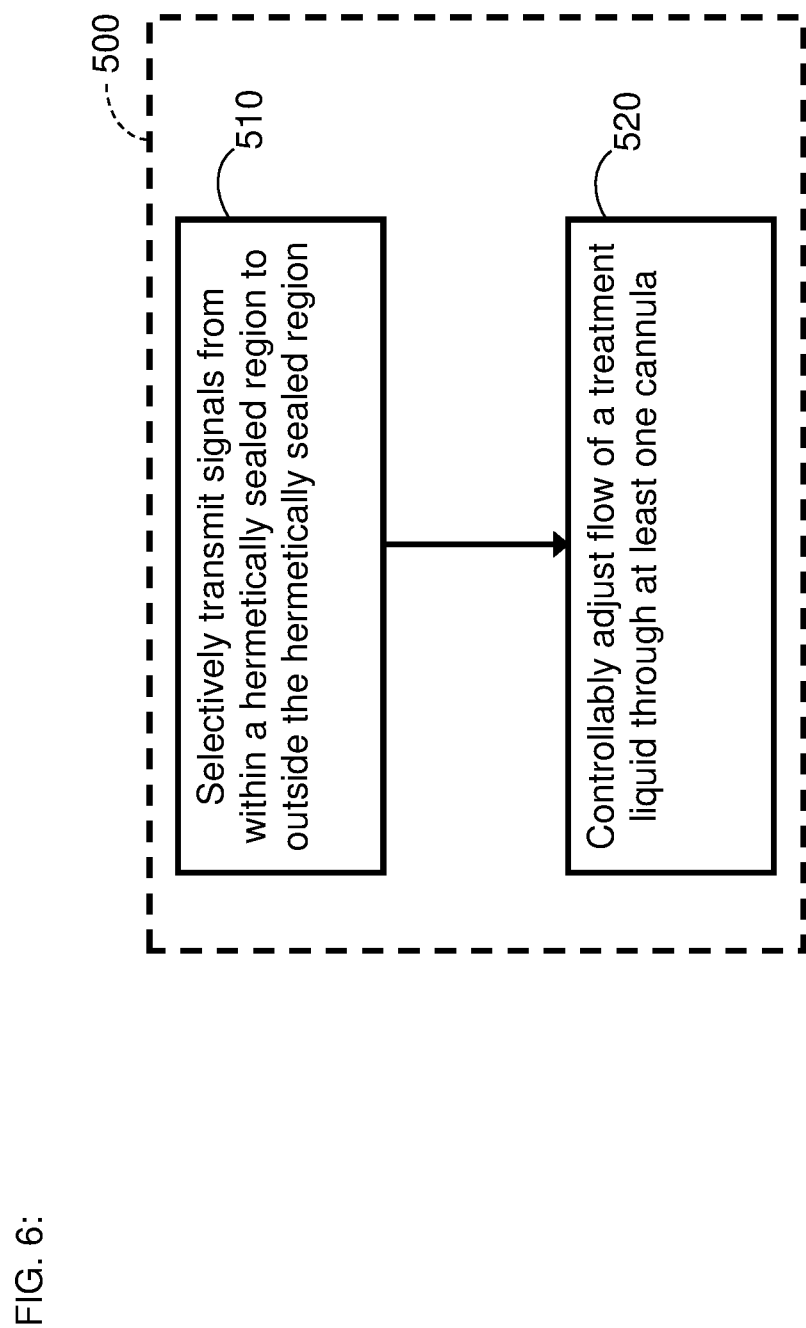
FIG. 6 is a flow diagram of an example method in accordance with certain embodiments described herein.

FIG. 6 is a flow diagram of an example method 500 in accordance with certain embodiments described herein. While the method 500 is described by reference to the example apparatus 200 of FIGS. 3A-3B and 4A-4C and the example heating elements 240 of FIGS. 5A-5D, other apparatus, elements, and structures are also compatible with the method 500. In an operational block 510, the method 500 comprises selectively transmitting signals from within a hermetically sealed region 220 to outside the hermetically sealed region 220. In an operational block 520, the method 500 further comprises controllably adjusting flow of a treatment liquid 262 through at least one cannula 260 in response to the signals. The hermetically sealed region 220 and the at least one cannula 260 are configured to be implanted on or within a recipient. In certain embodiments, the at least one cannula 260 is in fluidic communication with at least one reservoir 340 of the treatment liquid 262, and the at least one reservoir 240 is configured to be implanted on or within the recipient.

In certain embodiments, the signals comprise electrical signals 232 (e.g., electrical current) generated by circuitry 230 within the hermetically sealed region 220 and received by at least one electrical resistor 244 outside the hermetically sealed region 220 (e.g., as schematically illustrated by FIGS. 2A, 5A, and 5C). In certain embodiments, the signals comprise heat 242 generated by at least one electrical resistor 244 within a wall portion sealing the hermetically sealed region 220, the heat 242 flowing to a region outside the hermetically sealed region 220 (e.g., as schematically illustrated by FIG. 5B). In certain embodiments, the signals comprise heat 242 generated by at least one electrical resistor 244 fully within the hermetically sealed region 220 (e.g., as schematically illustrated by FIG. 2B), the heat 242 flowing to a region outside the hermetically sealed region 220.

In certain embodiments, controllably adjusting the flow comprises selectively applying heat 242 to a phase-change material 252 in mechanical communication with a corresponding portion of the at least one cannula 260. For example, the phase-change material 252 can be a portion of at least one flow control element 250 (e.g., as schematically illustrated by FIGS. 3A-3B and 4A-4C). For example, the phase-change material 252 can be responsive to the heat 242 by changing from a first phase that does not compress the corresponding portion of the at least one cannula 260 to a second phase that compresses the corresponding portion of the at least one cannula 260. For another example, the phase-change material 252 can be responsive to the heat 242 by changing from a first phase that compresses the corresponding portion of the at least one cannula 260 to a second phase that does not compress the corresponding portion of the at least one cannula 260. For another example, the phase-change material 252 can be a portion of the liquid 262 within the at least one cannula 260, the portion of the treatment liquid 262 expanding into a gas in response to the heat 242. In certain embodiments, controllably adjusting the flow further comprises ceasing applying the heat 242 to the phase-change material 252 (e.g., such that the phase-change material 252 converts back to the first phase; condenses back into a liquid).

In certain embodiments, controllably adjusting the flow comprises selectively compressing portions of the at least one cannula 260 to peristaltically pump the treatment liquid 262 through the at least one cannula 260. In certain embodiments, controllably adjusting the flow comprises selectively compressing at least one portion of the at least one cannula 260 to gate flow of the treatment liquid 262 through an outlet port of the at least one cannula 260.

It is to be appreciated that the embodiments disclosed herein are not mutually exclusive and may be combined with one another in various arrangements.

The invention described and claimed herein is not to be limited in scope by the specific example embodiments herein disclosed, since these embodiments are intended as illustrations, and not limitations, of several aspects of the invention. Any equivalent embodiments are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example embodiments disclosed herein, but should be defined only in accordance with the claims and their equivalents.

What is claimed is:

1. An apparatus comprising:
   an enclosure containing a hermetically sealed region and a non-hermetically sealed region, the enclosure configured to be implanted on or within a recipient;
   circuitry within the hermetically sealed region, the circuitry configured to generate signals;
   at least one heating element configured to receive the signals and to generate heat in response to the signals; and
   at least one flow control element within the non-hermetically sealed region, the at least one flow control element configured to respond to the heat by controlling a flow of liquid through at least one cannula.

2. The apparatus of claim 1, wherein the liquid comprises at least one medicament and the flow of the liquid through the at least one cannula comprises controlled administration of the at least one medicament internally to the recipient.

3. The apparatus of claim 1, wherein the liquid comprises a body liquid from the recipient and the flow of the liquid through the at least one cannula comprises controlled sampling of the body liquid internally from the recipient.

4. The apparatus of claim 1, wherein the non-hermetically sealed region comprises at least one non-hermetic cavity containing the at least one cannula.

5. The apparatus of claim 4, wherein the at least one non-hermetic cavity further contains at least one liquid reservoir, the at least one cannula in fluidic communication with the at least one liquid reservoir and the recipient.

6. The apparatus of claim 1, wherein the at least one heating element comprises at least one electrical resistor within the hermetically sealed region and in electrical communication with the circuitry.

7. The apparatus of claim 1, wherein the at least one heating element comprises at least one electrical resistor outside the hermetically sealed region, and the apparatus further comprises a plurality of electrical feedthroughs extending through a wall of the enclosure and in electrical communication with the circuitry and the at least one electrical resistor.

8. The apparatus of claim 1, wherein the at least one flow control element comprises a phase-change material configured to respond to the heat by changing from a first phase having a size with a first magnitude to a second phase having a size with a second magnitude different from the first magnitude.

9. The apparatus of claim 8, wherein the at least one flow control element is configured to allow flow of the liquid through a corresponding portion of the at least one cannula when the phase-change material is in the first phase and is further configured to not allow flow of the liquid through the corresponding portion of the at least one cannula when the phase-change material is in the second phase.

10. The apparatus of claim 1, wherein the at least one heating element comprises at least one electrical resistor embedded within a wall portion separating the hermetically sealed region from the non-hermetically sealed region.

11. The apparatus of claim 1, wherein the at least one flow control element comprises a phase-change material that surrounds a portion of the at least one cannula.

12. The apparatus of claim 11, wherein the at least one heating element surrounds the phase-change material.

13. The apparatus of claim 12, wherein the at least one heating element comprises a cuff electrode and an electrical resistor extending around the phase-change material.

14. The apparatus of claim 13, wherein the at least one flow control element further comprises a heating jacket extending around a perimeter of the phase-change material and configured to constrain the perimeter of the phase-change material from expanding radially outward from the at least one cannula.

15. The apparatus of claim 13, wherein the at least one flow control element further comprises a heating jacket extending over end portions of the phase-change material and configured to constrain the phase-change material from expanding longitudinally along the at least one cannula.

16. An apparatus comprising:
    an enclosure containing a hermetically sealed region, the enclosure configured to be implanted on or within a recipient;
    circuitry within the hermetically sealed region, the circuitry configured to generate signals;
    at least one heating element configured to receive the signals and to generate heat in response to the signals; and
    at least one flow control element outside the hermetically sealed region, the at least one flow control element comprising a phase-change material configured to respond to the heat by changing from a first phase having a size with a first magnitude to a second phase having a size with a second magnitude different from the first magnitude, the at least one flow control element configured to respond to the heat by controlling a flow of liquid through at least one cannula, wherein the phase-change material comprises at least some of the liquid within the at least one cannula.

17. The apparatus of claim 16, wherein the at least one flow control element is integrated with the at least one cannula.

18. The apparatus of claim 16, wherein the at least one flow control element comprises a portion of the at least one cannula.

19. The apparatus of claim 16, wherein the at least one heating element is configured such that the heat generated by the at least one heating element causes a phase change of the at least some of the liquid, creating a bubble within the at least one cannula.

20. An apparatus comprising:
   an enclosure containing a hermetically sealed region, the enclosure configured to be implanted on or within a recipient;
   circuitry within the hermetically sealed region, the circuitry configured to generate signals;
   at least one heating element configured to receive the signals and to generate heat in response to the signals; and
   at least one flow control element outside the hermetically sealed region, the at least one flow control element configured to respond to the heat by controlling a flow of liquid through at least one cannula, wherein the at least one flow control element comprises a plurality of flow control elements in mechanical communication with the at least one cannula, each flow control element of the plurality of flow control elements configured to be selectively actuated to peristaltically pump the liquid through the at least one cannula.

21. The apparatus of claim 20, wherein the flow control elements are positioned along the at least one cannula.

22. The apparatus of claim 21, further comprising at least one reservoir configured to contain the liquid and in fluidic communication with the at least one cannula, the at least one cannula comprising at least one outlet port configured to emit the liquid, wherein the flow control elements are positioned between the at least one reservoir and the at least one outlet port.

23. The apparatus of claim 20, wherein the flow control elements are configured to be sequentially actuated to peristaltically pump the liquid at a pumping rate in a range of 10 nanoliters/minute to 500 nanoliters/minute.

* * * * *